United States Patent [19]

Sollish et al.

[11] 4,025,165

[45] May 24, 1977

[54] ELECTRO OPTICAL IMAGING DEVICE

[75] Inventors: Bruce D. Sollish; Ephraim H. Frei, both of Rehovot, Israel

[73] Assignee: Yeda Research & Development Co. Ltd., Rehovot, Israel

[22] Filed: Sept. 30, 1975

[21] Appl. No.: 618,053

[30] Foreign Application Priority Data

Oct. 4, 1974   Israel .................................... 45787

[52] U.S. Cl. ........................... 350/161 S; 340/5 H
[51] Int. Cl.² .......................................... G01S 9/66

[58] Field of Search ............ 350/160, 161; 340/5 H

[56] References Cited

UNITED STATES PATENTS 3,736,552   5/1973   Sessler et al. ...................... 340/5 H Primary Examiner—William L. Sikes
Attorney, Agent, or Firm—Browdy and Neimark

[57] ABSTRACT

The present invention relates to an electro-optical imaging device containing as transducer a foil electret, having a transparent conducting backplate.

12 Claims, 4 Drawing Figures

ELECTRO OPTICAL IMAGING DEVICE

FIELD OF THE INVENTION

The present invention relates to a novel acousto-optical device. More particularly, it relates to a novel acousto-optical device based on the use of an electret or a material with similar electrical properties. The novel device is characterized in that it makes possible direct acousto-optical conversion without any intermediate stages, it has real-time capability of imaging for the observation of moving objects. The device can be positioned in any desired plane and can be operated at solid, at liquid or at gas interfaces. According to a preferred embodiment of the invention, means are provided for selecting the target plane which is viewed. Other and further features of the invention will become apparent hereinafter.

BACKGROUND OF THE INVENTION

For many years electrostatic principles have been employed in the generation and reception of acoustic energy. Devices based on electrostatics include the electrostatic loudspeaker and the condenser microphone. Such devices consist of three basic elements: (1) a rigid, electrically conducting backplate; (2) a flexible, electrically conducting diaphragm; (3) one or more mechanically compliant dielectric layers. These three elements are arranged in sandwich form with the dielectric in the middle. An electric bias voltage applied across the two conducting elements generates an electrostatic force which is balanced by the mechanical restoring force of the dielectric, establishing an equilibrium separation between the diaphragm and the backplate. For acoustic generation, the bias voltage has superimposed on it a time-varying voltage causing the diaphragm to vibrate. For acoustic reception, the time-varying voltage across the diaphargm and backplate is proportional to the vibration of the diaphragm in response to an incident acoustic field.

In order to reduce or eliminate the required dc bias voltage (which may be several hundred volts), an electrostatic device may be built with an electret as a dielectric element. Electrets, which are polarized dielectrics, can be formed in various ways, one of which will be described later. Using an electret in a condenser microphone results in an electret microphone in which the electret, rather than an external voltage source, generates the necessary electrostatic force.

Electrostatic devices, with or without electrets, have been widely used for audio applications. In such cases, the acoustic wavelength is larger than the lateral dimensions of the devices. Thus it can be assumed that the diaphragm vibrates uniformly as a sound piston.

For acoustic imaging purposes, energy in the ultrasonic region is utilized. The acoustic wavelength is usually much smaller than the detector lateral dimension. When a target is illuminated with an ultrasonic beam, the target attenuates part and scatters the rest of the beam. Hence the sound reflected from or transmitted through the target is, in general, no longer of uniform amplitude and phase. Instead, the beam is modulated, in both amplitude and phase, on a point-by point basis.

It is a well-known result of diffraction theory that if the point-by-point amplitude and phase of a field scattered by a target can be detected on some plane, and if this amplitude and phase distribution can be recorded and reproduced, an image of the target can be reconstructed. Further, if the incident field is acoustically derived, while the playback is optical, then an optical reproduction of the acoustically-illuminated target is generated. This is the basis of acoustical holography.

STATE OF THE PRIOR ART

The problem of acoustic-optical imaging has been approached in many different ways. Our method is superficially similar to some of them; however, a brief presentation will show that the differences are substantial.

1. Electrostatic detector — such devices are scaled-down versions of audio-electrostatic detectors. The magnitude and phase of the acoustic field at a point in space is determined by placing the detector at that point and measuring and recording the resultant voltage output of the detector. The detector can be mechanically scanned across the detection plane on a point-by-point basis to record the amplitude and phase information over a plane of many wavelengths for reconstructing an image. However, the process of scanning can be quite slow and useless for real-time observation of the target in motion.

Another solution is to use an array of electrostatic detectors. Scanning and recording the output of each electrostatic element is accomplished electronically. This can be done more rapidly than mechanical scanning. However, the price paid is in electronic complexity, which ultimately limits the maximum number of array elements.

2. Laser-scanned diaphragm — in this method a single thin metallized diaphragm placed in the scattered acoustic field is the detecting element. Each point of the diaphragm vibrates in amplitude and phase according to the incident acoustic pressure. A laser beam scans the back of the diaphragm on a point-by-point basis. Light reflected from each point is phase-modulated, the phase modulation being a function of both the amplitude and phase of the local diaphragm displacement. The phase-modulated reflected light undergoes optical heterodyning with an unmodulated reference beam, electronic detection and processing to finally be applied in modulating a writing laser beam, scanned in synchronism with the reading laser beam to generate a hologram.

This method is rather complicated both electronically and optically. The main problem is that the diaphragm surface deformation is a lenear function of the incident acoustic pressure. The time-average displacement at any point is thus zero. It can be shown that only a diaphragm displacement witha dc or slowly-varying component proportional to the incident acoustic field can properly modulate the light beam for direct acous-to-optical conversion. Since there is no such dc component, the laser-scanned diaphragm method requires an additional optical reference, resulting in a complicated acousto-electronic-optical conversion system.

3. Liquid surface imaging — This is a method of acousto-optical imaging that does not require any intermediate electronic processing. The detector is a liquid surface which is elevated on a point-by-point basis proportionally to the radiation pressure of an acoustic field directed towards the liquid-air interface. The acoustic field consists of an unmodulated reference acoustic beam and a signal beam spatially modulated in amplitude and phase by transmission through a target Since radiation pressure is proportional to the square o the acoustic pressure, the liquid surface is a square-law detector. Thus there is a time-invarient component of the liquid surface elevation proportional to the local signal amplitude and phase. If the liquid surface is illuminated with a coherent light beam, one of the optical side-bands reflected from the surface is an optical version of the acoustic target. Filtering out all other light allows the viewer to see the reconstructed image.

The liquid surface method is a direct acousto-optical method that enables real-time imaging. However, there are several disadvantages;

a. Since a liquid-air interface is the detector, the target must either be immersed in liquid, or else elaborate coupling methods must be used if the target must not or cannot be immersed.

b. Since the liquid-air interface is inherently mechanically unstable, precautions must be taken to isolate the liquid surface from all external sources of vibration. Typically, the target is placed in a heavy main tank, while the detection surface is in a light auxiliary tank.

c. This method uses transmission-type acoustic imaging, whereas it may be desirable to provide reflection type imaging as well.

d. The liquid surface is always horizontal, whereas it may be desirable to place the detector in some other plane.

DESCRIPTION OF THE INVENTION

The present invention relates to an acousto-optical detector that is an improvement over the above types of detectors. It relates to an electrostatic device employing an electret as the active element. Also unpolarized dielectrics with applied dc biasing can be used. The backplate is made of transparent optically-flat conducting glass. This give optical access to the foil electret diaphragm. The foil electret adheres closely to the conducting side of the glass backplate. The sandwich of foil electret and glass backplate is sealed round the edges. The foil is coated with an insulating chemically inert polymer layer such as Teflon. Electric access is through leads cemented to the diaphragm and to the backplate. The surface displacement can be enhanced by constructing an electret of non-uniform density in the thickness direction. In the manufacture of the dielectric, minute air bubbles can be impregnated in the dielectric material in such a way that the density of the electric decreases along the thickness direction. Then the acoustic wave entering the dielectric is totally reflected by the time it reaches the end of the dielectric. Total reflection gives maximum displacement amplitude and hence maximum detector sensitivity. The response of the novel detector to an incident acoustic field is a linear point-by-point function of the pressure amplitude and phase. Therefore, ordinarily the diaphragm surface displacement has a time-average value of zero. However, applying a sine-wave readout voltage of the detector modulates the effective elastance of the dielectric layer. If at the same time an acoustic wave strikes the diaphragm, it meets a mechanical system with time-varying elastance.

The resultant displacement of the diaphragm contains a component proportional to the product of the acoustic and electric excitations. If the frequency of the applied readout signal is equal to that of the incident acoustic field scattered by the target, the displacement of each point of the diaphragm contains a dc component proportional to the local amplitude and phase of the incident acoustic pressure. The diaphragm deflection is therefore similar to that in the liquid-air interface method of acoustical imaging.

An optical image is reconstructed by directing coherent light through the transparent backplate when the detector receives an acoustic signal and a readout signal simultaneously. One of the optical sidebands reflected back from the diaphragm contains information about the acoustic field. This sideband is optically filtered to reconstruct an image of the target.

One feature of our invention is the ability to utilize strobed readout for selecting a single plane of the target for viewing when pulsed cw reflection-type imaging is employed. At some time after emission of the insonifying pulse, scattered sound from a particular plane through the target reaches the detector. If a readout voltage is applied only when the detector surface receives energy from that plane, only that particular plane is imaged. Varying the time delay between the insonifying pulse and the readout pulse to the detector changes the plane of the target viewed. Naturally, cw insonification of the target and continuous application of a readout voltage to the detector enables transmission-type imaging to be achieved.

One of the main applications of the acousto-optical imaging device is in non-destructive testing. Faulty welds between surfaces and internal flaws within relatively homogeneous casting can be imaged in real-time. The detector and part to be examined are either placed in a liquid bath, or the detector can be used for contact-scanning a smooth-surfaced target. The real-time imaging property of the detector allows continuous inspection of parts as they pass by.

Another application of the acousto-optical imaging device is in medical diagnosis, for visualizing internal atructure and organs and for detecting and identifying pathologies. Depending on the application either immersion or contact methods can be utilized. Real-time imaging allows examination of moving structures, such as the human heart or an active fetus. The electronic focusing feature of the imaging device enables the physician to zero-in on the precise plane of interest in which the structure of pathology is best presented.

BRIEF DESCRIPTION OF THE DRAWINGS

Certain specific embodiments of the invention are illustrated with reference to the enclosed schematical drawings, in which.

DESCRIPTION OF THE PREFERRED EMBODIMENT

Figure 1:
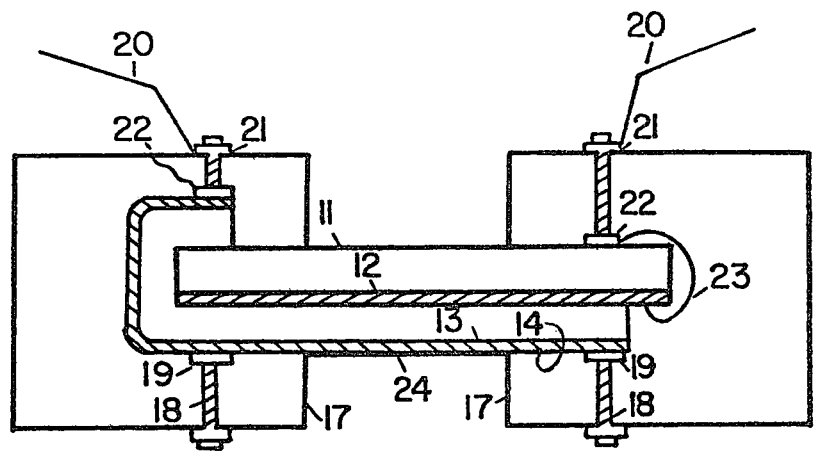
FIG. 1 is a schematical side-view, in section, of a transducer used in a device according to the invention.

The novel transducer device is illustrated in FIG. 1. A conducting non-reflecting glass backplate 11, is mounted with its conducting layer 12 facing the electret 13, whose conducting layer 14 faces away from the glass backplate 11. Electrostatic attraction causes the polymer electret 13 and its conducting layer 14 to adhere strongly to the conducting surface of the glass backplate 11. The backplate 11 and polymer foil electret 13 are secured at their edges by a pair of insulating retaining blocks 17 made of laminated phenolic plastic. These are fastened from below by metal screws 18 electrically insulated from the foil electret 13 by mica standoffs 19. Two leads 20 to a supply device are brough off from a pair of binding posts 21 which also serve as upper retaining screws. These screws are electrically connected respectively to the foil conducting layer 14, which acts as one electrode, and to the conducting backplate 11, which acts as the other, by means of copper conducting washers 22, one of which is in direct contact with the layer 14, the other of which is connected to the conducting layer 12 via a wire 13, secured to the conducting layer 12 by conducting glue. The detector is sealed around the edges with cement and a protective Teflon layer 24 is deposited on the exposed aluminum layer of the diaphragm to prevent chemical contamination and to provide electrical insulation.

The glass backplate 11 is 50 mm × 50 mm × 1 mm optically flat glass with a uniform 0.15 um thick transparent conducting coating. The foil electret 13 is a 25 um-thick ploymer layer (Dupont Mylar) coated on one side with a 1 um aluminum layer 14. The retaining blocks 17 are each 20 mm × 20 mm × 50 mm. Two more retaining blocks (not shown), each 20 mm × 20 mm × 30 mm, provide additional clamping at the other two edges of the detector. The total sensitive surface area of the detector is 30 mm × 30 mm. The detector could easily be made larger, since conducting glass plates larger than 100 mm × 100 mm are commercially available.

The electret itself is prepared using a standard thermal technique. A 100 mm square piece of polymer foil is placed between two parallel aluminum electrodes, each 60 mm square. The electrodes are separated by 5 mm. The above arrangement is placed in an oven and heated to 130 ° C. When the polymer softens, a 5KV voltage is connected between the electrodes, generating a polarizing field in the polymer. The arrangement is then left to cool off slowly to room temperature. The external electrodes are removed. The polymer foil thereafter retains its polarization, i.e. it has been made into an electret.

Although there are many possible arrangements of our detector for acousto-optical, two particualr examples are schematically shown here.

C.W. TRANSMISSION MODE IMAGING

Figure 2:
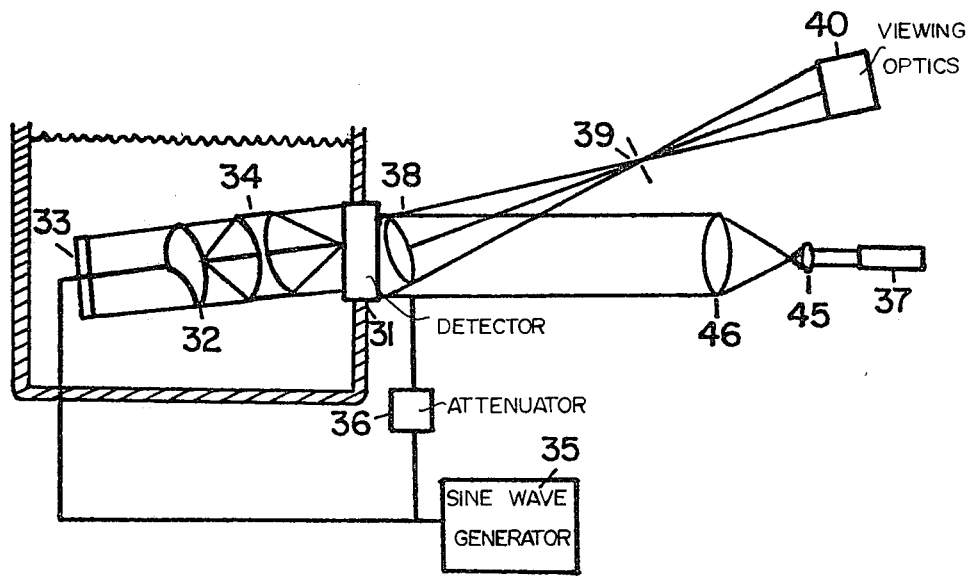
FIG. 2 is a schematical side-view and block-diagram of a device according to the invention.

The configuration is shown in FIG. 2. The detector 31 is rigidly mounted in the side of a water tank, glass backplate out of the water facing right and the foil diaphragm in the water facing left. A target 32 is placed approximately 10 cm to the left of the detector. A plane wave ultrasonic transducer 33 is placed another 5-10 cm. to the left of the target 32, and inclined at 10° to the normal to the detector. An acoustic condensing lends 34 projects an image of the target on the detector surface. For thin targets, the acoustic lens can be eliminated and the target placed close to the detector. A sinewave generator 35 (0–500V, 1–10 OMH) supplies both an excitation voltage of the transducer and, through an attenuator 36 (0–40 db) a readout signal to the detector.

A 1W Ar-ion laser 37 positioned behind a spatial filtering means 45 and collimation 46 illuminates the diaphragm surface through the glass backplate. The light reflected at an angle of 10° is focused by a condensing lens 38. A pinhole aperture 39 at the lens focal point filters out unwanted light, and standard viewing optics 40 gives an optical image of the plane focused on the detection surface. The image can be viewed directly, photographed or displayed in a closed-circuit TV system.

PULSED CW REFLECTION-MODE IMAGING

Figure 3:
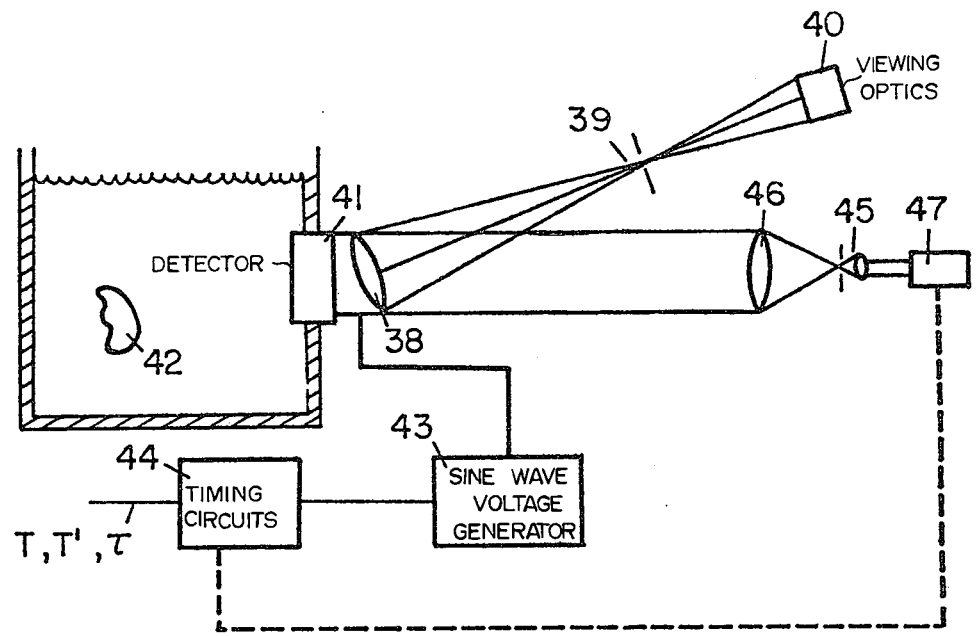
FIG. 3 is a schematical side-view of an embodiment of pulsed cw reflection mode imaging according to the present invention.

This configuration is shown in FIG. 3. Here also the detector 41 is mounted on the side of a water tank and a target 42 is placed to the left. The detector 41 serves as both transmitter and receiver.

Figure 4:
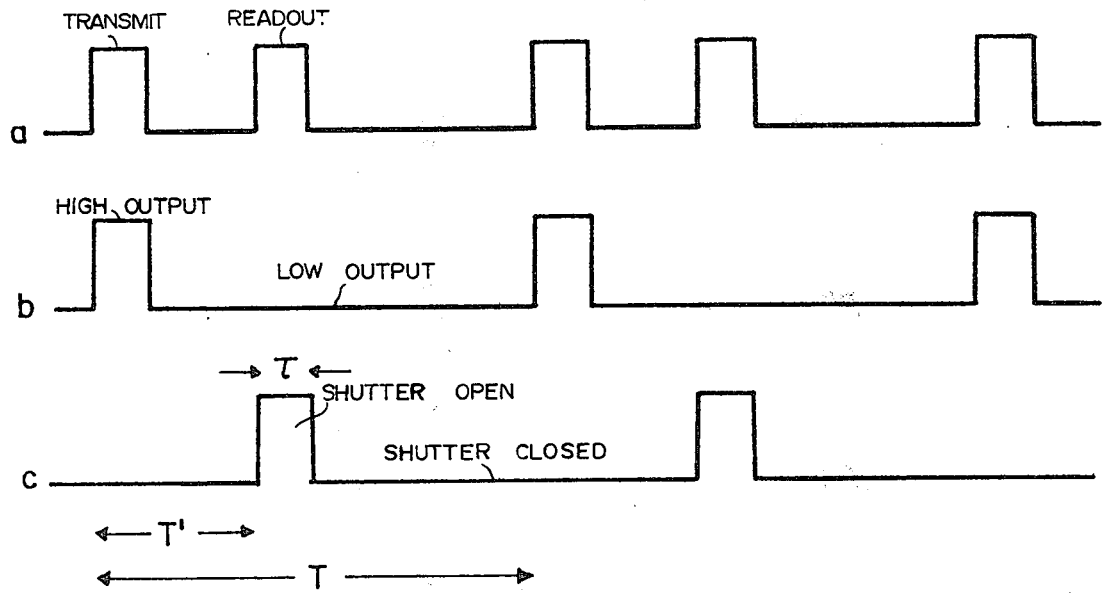
FIG. 4 is a wave form diagram, helpful in understanding the embodiment shown in FIG. 3.

An externally-triggered sinewave voltage generator 43 with externally-controlled amplitude 43 supplies the driving voltage to the electret device for generation of an ultrasonic beam and also supplies an attenuated readout voltage to the detector at the appropriated intervals. An electronics black-box 44 contains the various timing circuits for generating control signals to the oscillator 43 and a circuit for varying the oscillator voltage output. Typical timing waveforms are shown in FIG. 4.

Optical readout of the detector is the same as in FIG. 2. However, a more powerful pulsed, laser 47 should be used since the image is readout for only a small portion of the cycle.

For non-destructive testing, the energy flux is adjusted according to the requirements of each individual case.

For diagnostic purposes in human medicine, an average intensity of not exceeding about 1 mW/cm$^2$, can be used.

It is to be appreciated that in place of the foil electret, an unpolarized dielectric foil provided with dc biasing could be used as well in the device of the present invention.

We claim:

1. In an acoustic-to-optical imaging device having a transducer responsive to an acoustic beam applied to one surface thereof and means for producing a viewable image, the improvement comprising as the transducer therein a foil electret, having an optically transparent conducting backplate as one of its electrodes and a second electrode.

2. An improved acoustic-to-optical device according to claim 1, wherein said electret has a foil of varying density in its thickness direction.

3. An improved acoustic-to-optical imaging device according to claim 1, including means coupled to said electret for supplying pulsed cw readout signals thereto to electronically focus the device.

4. An improved acoustic-to-optical imaging device according to claim 1, including means for illuminating a surface of said electret through said optically transparent backplate, said means for illuminating including a light source, spatial filtering means and collimation means positioned in reversed serial order from said transducer, and a condensing lens for focussing reflected light from said foil electret to give the desired image.

5. An improved acoustic-to-optical imaging device according to claim 1, wherein said light source is a laser.

6. In an acoustic-to-optical imaging device having a transducer responsive to an acoustic beam applied to one surface thereof and means for producing a viewable image, the improvement comprising as the transducer therein an unpolarized dielectric foil electret having an optically transparent conducting backplate as one of its electrodes, a second electrode, and means for applying a d.c. bias voltage across said first and second electrodes.

7. An improved acoustic-to-optical device according to claim 6, wherein said foil is of varying density in its thickness direction.

8. An improved acoustic-to-optical imaging device according to claim 6, including means coupled to said foil for supplying pulsed cw readout signals thereto to electronically focus the device.

9. An improved acoustic-to-optical imaging device according to claim 6, including means for illuminating a surface of said foil through said optically transparent backplate, said means for illuminating including a light source, spatial filtering means and collimation means positioned in reversed serial order from said transducer, and a condensing lens for focussing reflected light from said foil to give the desired image.

10. An improved acoustic-to-optical imaging device according to claim 6, wherein said light source is a laser.

11. A method of providing an optical image comprising:
positioning a foil electret having an optically transparent conducting backplate in vicinity of possible targets to be imaged;
illuminating one surface of said electret with a coherent light beam;
illuminating a surface of said electret opposite said one surface with an acoustic beam; and
developing an image from light reflected from said one surface.

12. A method of providing an optical image comprising:
positioning an unpolarized dielectric foil having an optically transparent conducting backplate in the vicinity of possible targets to be imaged;
supplying a d.c. voltage to said foil;
illuminating one surface of said dielectric foil with a coherent light beam;
illuminating a surface of said dielectric foil opposite said one surface with an acoustic beam; and
developing an image from light reflected from said one surface.

* * * * *